United States Patent [19]
Matsuo et al.

[11] Patent Number: 5,939,413
[45] Date of Patent: Aug. 17, 1999

[54] PIPERAZINE DERIVATIVES

[75] Inventors: Masaaki Matsuo, Toyonaka; Daijiro Hagiwara, Moriguchi; Takashi Manabe, Kawanishi; Nobukiyo Konishi, Nagaokakyo; Shinji Shigenaga, Kobe; Kenji Murano; Hiroshi Matsuda, both of Osaka; Hiroshi Miyake, Kyoto, all of Japan

[73] Assignee: Fujisawa Pharmaceutical Co., Ltd., Osaka, Japan

[21] Appl. No.: 08/952,112

[22] PCT Filed: May 21, 1996

[86] PCT No.: PCT/JP96/01334

§ 371 Date: Nov. 24, 1997

§ 102(e) Date: Nov. 24, 1997

[87] PCT Pub. No.: WO96/37488

PCT Pub. Date: Nov. 28, 1996

[30]  Foreign Application Priority Data

May 25, 1995 [GB] United Kingdom ............... 9510600

[51] Int. Cl.⁶ ............... A61K 31/55; A61K 31/495; C07D 403/06; C07D 403/14
[52] U.S. Cl. ............... 514/218; 514/232.5; 514/235.2; 514/253; 514/254; 540/575; 544/121; 544/357; 544/364; 544/373
[58] Field of Search ............... 544/373, 121, 544/357, 364; 514/253, 254, 218, 232.5, 235.2; 540/575

[56] References Cited

U.S. PATENT DOCUMENTS

| | | | |
|---|---|---|---|
| 4,598,079 | 7/1986 | Beyerle et al. | 544/373 |
| 5,670,505 | 9/1997 | Matsuo et al. | 514/253 |

FOREIGN PATENT DOCUMENTS

| | | |
|---|---|---|
| 0072932 | 3/1983 | European Pat. Off. . |
| 2271774 | 4/1994 | United Kingdom . |

OTHER PUBLICATIONS

Frossard et al, *Life Sciences* vol. 49, pp. 1941–1953 (1991).

*Primary Examiner*—Emily Bernhardt
*Attorney, Agent, or Firm*—Oblon, Spivak, McClelland, Maier & Neustadt, P.C.

[57] ABSTRACT

This invention relates to piperazine derivatives of the formula:

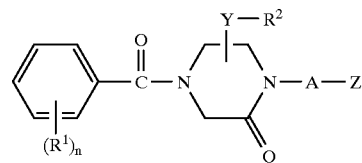

wherein each symbol is as defined in the description, and its pharmaceutically acceptable salt, to processes for preparation thereof, to pharmaceutical composition comprising the same, and to a use of the same for treating or Tachykinin-mediated diseases in human beings or animals.

5 Claims, No Drawings

PIPERAZINE DERIVATIVES

TECHNICAL FIELD

The present invention relates to new piperazine derivatives and a pharmaceutically acceptable salt thereof.

More particularly, it relates to new piperazine derivatives and a pharmaceutically acceptable salt thereof which have pharmacological activities such as Tachykinin antagonism, especially Substance P antagonism, Neurokinin A antagonism, Neurokinin B antagonism, and the like, to a process for preparation thereof, to a pharmaceutical composition comprising the same, and to a use of the same as a medicament.

Accordingly, one object of the present invention is to provide new and useful piperazine derivatives and a pharmaceutically acceptable salt thereof which have pharmacological activities such as Tachykinin antagonism, especially Substance P antagonism, Neurokinin A antagonism, Neurokinin B antagonism, and the like.

Another object of the present invention is to provide a process for the preparation of said piperazine derivatives and a salt thereof.

A further object of the present invention is to provide a pharmaceutical composition comprising, as an active ingredient, said piperazine derivatives and a pharmaceutically acceptable salt thereof.

Still further object of the present invention is to provide a use of said piperazine derivatives or a pharmaceutically acceptable salt thereof as Tachykinin antagonist, especially Substance P antagonist, Neurokinin A antagonist or Neurokinin B antagonist, useful for treating or preventing Tachykinin-mediated diseases, for example, respiratory diseases such as asthma, bronchitis, rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g., migraine, headache, toothache, cancerous pain, back pain, etc.); and the like in human being or animals.

DISCLOSURE OF INVENTION

The object compound of the present invention can be represented by the following general formula (I):

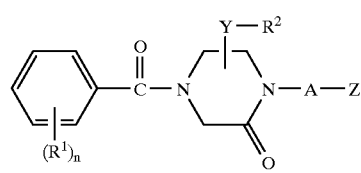

wherein

Y is bond or lower alkylene;

$R^1$ is halo(lower)alkyl;

$R^2$ is indolyl which may have 1, 2 or 3 suitable substituent s);

A is bond or lower alkylene;

Z is hydrogen, carboxy, protected carboxy or a group of the formula:

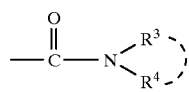

in which $R^3$ and $R^4$ are independently hydrogen or a N containing saturated heterocyclic group which may be substituted by 1 to 3 and same or different suitable substituent (s), or $R^3$ and $R^4$ together with the adjacent nitrogen atom form a N containing saturated heterocyclic group which may be substituted by 1 to 3 and same or different suitable substituent(s); and n is 0, 1 or 2; provided that when n is more than 1, $R^1$ may be the same or different group; or its pharmaceutically acceptable salt.

According to the present invention, the object compound (I) or a salt thereof can be prepared by processes which are illustrated in the following schemes.

Process 1

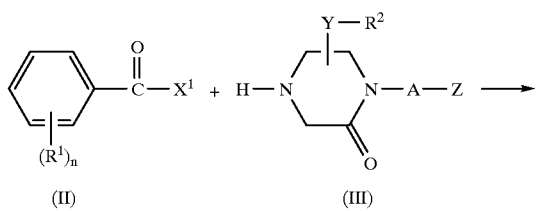

Process 2

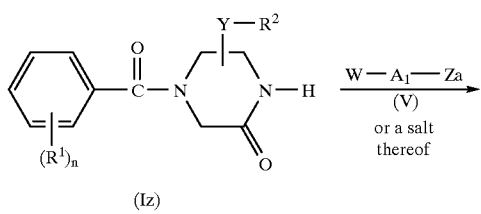

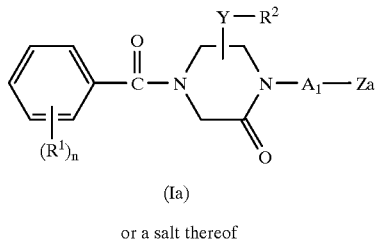

(Ia)

or a salt thereof

Process 3

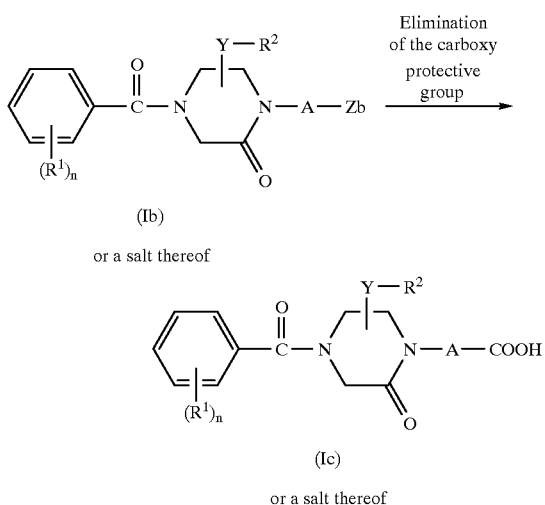

Process 4

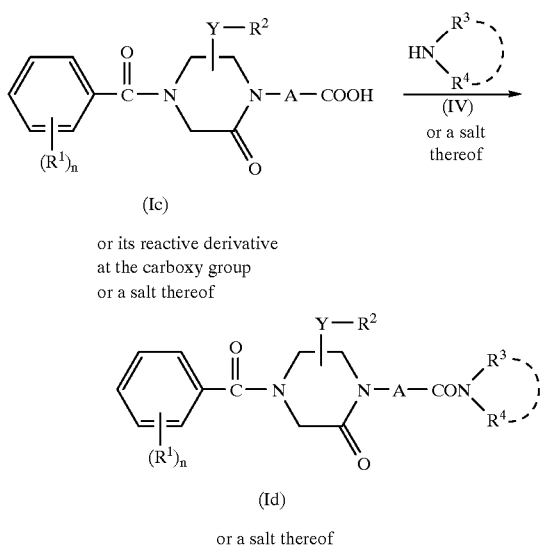

or a salt thereof wherein

A, Y, Z, R¹, R², R³, R⁴ and n are each as defined above;

X¹ is a leaving group;

Za is carboxy, protected carboxy or a group of the formula:

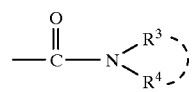

in which $R^3$ and $R^4$ are the same as above;

Zb is protected carboxy;

$A_1$ is lower alkylene; and

W is a leaving group.

As to the starting compounds (II) and (III), some of them are novel and can be prepared by the procedures described in the Preparations and Examples or an equivalent procedures thereof, or a conventional manner.

Suitable salts and pharmaceutically acceptable salts of the starting and object compounds are conventional non-toxic salt and include an acid addition salt such as an organic acid salt (e.g. acetate, trifluoroacetate, fumarate, maleate, tartrate, methanesulfonate, benzenesulfonate, formate, toluenesulfonate, etc.), an inorganic acid salt (e.g. hydrochloride, hydrobromide, hydroiodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention include within the scope thereof are explained in detail as follows.

The term "lower" is intended to mean 1 to 6, preferably 1 to 4 carbon atom(s), unless otherwise indicated.

Suitable "lower alkylene" is straight or branched one having 1 to 6 carbon atom(s) and includes methylene, ethylene, trimethylene, propylene, tetramethylene, methylmethylene, methyltrimethylene, hexamethylene, and the like, in which the preferred one is methylene, ethylene, trimethylene or methylmethylene.

The term "halogen" is fluoro, chloro, bromo and iodo.

Suitable "lower alkyl" is straight or branched one having 1 to 6 carbon atom(s) and includes methyl, ethyl, propyl, isopropyl, butyl, isobutyl, pentyl, hexyl and the like.

Suitable "halo (lower) alkyl" includes chloromethyl, bromomethyl, fluoromethyl, iodomethyl, trifluoromethyl, dichloromethyl, 2-fluoroethyl, 1-chloroethyl, 2-chloroethyl and the like, in which the preferred one is trifluoromethyl.

n is 0, 1 or 2, and more preferable one is 1 or 2. When the n is 2, $R^1$ may be the same or different group.

The "indolyl" group in the definition of $R^2$ may be bonded to the adjacent "Y" in the formula (I) at the carbon atom or the hetero atom in the indolyl group.

"Suitable substituent(s)" of the "indolyl" group for $R^2$ includes lower alkyl, halogen, halo(lower)alkyl, amino, (mono- or di-)lower alkylamino(lower)alkyl (e.g., 2-dimethylaminoethyl, etc.) and the like.

Suitable "protected carboxy" includes esterified carboxyl groups.

Suitable examples of the ester moiety of "esterified carboxy" are, for instance, lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester) which may have one or more suitable substituents such as lower alkanoyloxy(lower)alkyl ester [e.g. acetoxvmethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, 3,3-dimethylbutyryloxymethyl ester, 1(or 2)-pentanoyloxyethyl ester], lower alkanesulfonyl(lower)alkyl ester [e.g. 2-mesylethyl ester], mono(or di or tri)-halo (lower)alkyl ester [e.g. 2-iodoethyl ester, 2,2,2-trichloroethyl ester], lower alkoxycarbonyloxy(lower)alkyl ester [e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester], phthalidylidene (lower)alkyl ester, or (5-lower alkyl-2-oxo-1,3-dioxol-4-yl) (lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester]; lower alkenyl ester [e.g. vinyl ester, allyl ester]; lower alkynyl ester [e.g. ethynyl ester, propynyl ester]; ar(lower)alkyl ester which may have one or more suitable substituents [e.g. benzyl ester, 4-methoxybenzyl ester, 4-nitrobenzyl ester, phenethyl ester, trityl ester, benzhydryl ester, bis(methoxyphenyl) methyl ester, 3,4-dimethoxybenzyl ester, 4-hydroxy-3,5-di-tert-butylbenzyl ester]; aryl ester which may have one or more suitable substituents [e.g. phenyl ester, 4-chlorophenyl ester, tolyl ester, tert-butylphenyl ester, xylyl ester, mesityl ester, cumenyl ester]; and phthalidyl ester.

Suitable "N containing saturated heterocyclic group" in the definition of $R^3$ and $R^4$ includes 5-, 6- or 7-membered saturated heterocyclic group and more preferable one is a N containing saturated heterocyclic group which contains at least one nitrogen atom as a hetero atom. Most preferable one is 1-pyrrolidinyl, 1-piperidyl, 4-morpholino, 1-piperazinyl, 1-homopiperazinyl, etc.

"Suitable substituent(s)" of the "N containing saturated heterocyclic group" in the definition of $R^3$ and $R^4$ includes lower alkyl, halogen, halo(lower)alkyl, oxo, amino and another "N containing saturated heterocyclic group" which is exemplified one in the definition of $R^3$ and $R^4$.

$R^3$ and $R^4$ together with the adjacent nitrogen atom may form a N containing saturated heterocyclic group which may be substituted by 1 to 3 and same or different suitable substituent(s). Suitable explanations and examples of the "N containing saturated heterocyclic group" which is formed by $R^3$, $R^4$ and the adjacent nitrogen atom and "suitable substituent(s) thereof" are the same as exemplified one in the definition of $R^3$ and $R^4$.

Suitable "leaving group" may include hydroxy, reactive group derived from hydroxy and the like.

Suitable "reactive group derived from hydroxy" may include acid residue and the like.

Suitable "acid residue" may include halogen (e.g. fluoro, chloro, bromo, iodo), acyloxy (e.g. acetoxy, tosyloxy, mesyloxy, etc.) and the like.

The Processes 1 to 4 for preparing the object compound (I) of the present invention are explained in detail in the following.

Process 1

The object compound (I) or a salt thereof can be prepared by reacting the compound (II) or a salt thereof with the compound (III) or its reactive derivative at the imino group or a salt thereof.

Suitable reactive derivative at the imino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethyl-silyl) acetamide, bis(trimethylsilyl)urea or the like; a derivative formed by reaction of the compound (III) with phosphorus trichloride or phosgene and the like.

The reaction is usually carried out in a conventional solvent such as water, alcohol [e.g. methanol, ethanol, etc.], acetone, dioxane, acetonitrile, chloroform, dichloromethane, dichloroethane, tetrahydrofuran, ethyl acetate, N,N-dimethylformamide, pyridine or any other organic solvent which does not adversely influence the reaction. These conventional solvents may also be used in a mixture with another solvent.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; pentamethyleneketene-N-cyclohexylimine; diphenylketene-N-cyclohexylimine; ethoxyacetylene; 1-alkoxy-1-chloroethylene; trialkyl phosphate; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxaozlium hydroxide intramolecular salt; 1-(p-chlorobenzenesulfonyloxy)-6-chloro-1H-benzotriazole; 1-hydroxybenzotriazole; so-called Mukaiyama reagent such as 2-chloro-1-methylpyridinium iodide; 1-(3-dimethylaminopropyl)-3-ethylcarbodiimide hydrochloride by itself or in combination with 1-hydroxybenzotriazole; so-called Vilsmeier reagent prepared by the reaction of N,N-dimethylformamide with thionyl chloride, phosgene, trichloromethyl chloroformate, phosphorus oxychloride, etc.; or the like, or the mixture thereof.

The reaction may also be carried out in the presence of an inorganic or organic base such as an alkali metal bicarbonate, tri(lower)alkylamine, pyridine, N-(lower) alkylmorpholine, N,N-di(lower)alkylbenzylamine, or the like.

The reaction temperature is not critical, and the reaction is usually carried out under cooling to warming.

Process 2

The object compound (Ia) or a salt thereof can be prepared by reacting the compound (Iz) or its reactive derivative at the imino group or a salt thereof with the compound (V) or a salt thereof.

Suitable example of the reactive derivative at the imino group of the compound (Iz) is the one as exemplified for compound (III) in the Process 1.

This reaction is usually carried out in a solvent such as alcohol [e.g. methanol, ethanol, etc.], dichloromethane, benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], alkali metal hydride [e.g. sodium hydride, potassium hydride, etc.], tri(lower)alkylamine [e.g. trimethylamine, triethylamine, diisopropylethylamine, etc.], pyridine or its derivative [e.g. picoline, lutidine, 4-dimethylamino-pyridine, etc.], or the like. In case that the base to be used in liquid, it can also be used as a solvent.

The reaction temperature is not critical, and the reaction can be carried out under cooling, at room temperature or under warming or heating.

Process 3

The compound (Ic) or a salt thereof can be prepared by subjecting the compound (Ib) or a salt thereof to an elimination reaction of the carboxy protective group.

The reaction is carried out in accordance with a conventional method such as hydrolysis, reduction or the like.

The hydrolysis is preferably carried out in the presence of a base or an acid includina Lewis acid. Suitable base may include an inorganic base and an organic base such as an alkali metal [e.g. sodium, potassium, etc.], an alkaline earth metal [e.g. magnesium, calcium, etc.], the hydroxide thereof or carbonate thereof or bicarbonate thereof, trialkylamine [e.g. trimethylamine, triethylamine, etc.], picoline, 1,5-diazabicyclo[4.3.0]non-5-ene, 1,4-diazabicyclo[2.2.2] octane, 1,8-dlazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], dichloromethane, tetrahydrofuran, a mixture thereof or any other solvent which does not adversely influence the reaction. A liquid base or acid can be also used as the solvent. The reaction temperature is not critical, and the reaction can be usually carried out under cooling, at ambient temperature or under warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical, and the reaction can be usually carried out under cooling, at ambient temperature or under warming.

Process 4

The compound (Id) or a salt thereof can be prepared by reacting the compound (Ic) or its reactive derivative at the carboxy group or a salt thereof with the compound (IV) or a salt thereof.

Suitable reactive derivative at the carboxy group of the compound (Ic) may include an acid halide, an acid anhydride, an activated amide, an activated ester, lower alkyl ester, and the like. Suitable examples of the reactive derivatives may be an acid chloride; an acid azide; a mixed acid anhydride within acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2{}^+N=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from the above according to the kind of the compound (Ic) to be used.

In this reaction, when the compound (Ic) is used in a free acid form or its salt form, the reaction is preferably carried out in the presence of a conventional condensing agent as exemplified in the Process 1.

This reaction can be carried out in substantially the same manner as the Process 1, and therefore the reaction mode and reaction conditions [e.g. solvents, reaction temperature, etc.] of this reaction are to be referred to those as explained in the Process 1.

It is to be noted that the compound (I) and the other compounds may include one or more stereoisomers due to asymmetric carbon atoms, and all of such isomers and mixture thereof are included within the scope of this invention.

For example, the object compound of the present invention represented by the general formula (I) contains two stereoisomers illustrated by the following general formulae ($I_R$) and ($I_S$), and these two isomers are included in this invention.

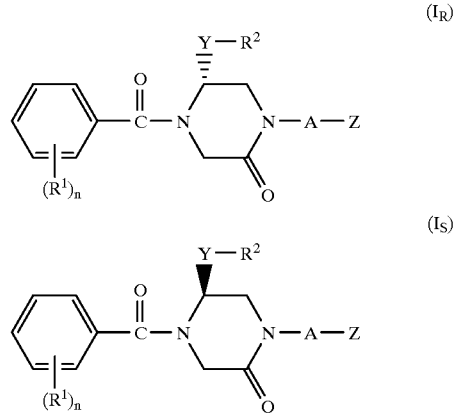

The object compound (I) and a pharmaceutically acceptable salt thereof have pharmacological activities such as Tachykinin antagonism, especially Substance P antagonism, Neurokinin A antagonism or Neurokinin B antagonism, and therefore are useful for treating or preventing Tachykinin-mediated diseases, particularly Substance P-mediated diseases, for example, respiratory diseases such as asthma, bronchitis (e.g. chronic bronchitis, acute bronchitis and diffuse panbronchiolitis, etc.), rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g. migraine, headache, cluster headache, toothache, cancerous pain, back pain, neuralgia, etc.); and the like.

Further, it is expected that the object compound (I) and a pharmaceutically acceptable salt thereof of the present invention are useful for treating or preventing ophthalmic diseases such as glaucoma, uveitis, and the like; gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, Raynaud's disease, and the like; epilepsy; spastic paralysis; pollakiuria; cystitis; bladder detrusor hyperreflexia; urinary incontinence; Parkinson diseases; dementia; AIDS related dementia; Alzheimer's diseases; Down's syndrome; Huntington's chorea; carcinoid syndrome; disorders related to immune enhancement or suppression; disorders caused by *Helicobacter pylori* or another spiral urease-positive gram-negative bacterium; sunburn; angiogenesis or diseases caused by angiogenesis; and the like.

It is furthermore expected that the object compound (I) and a pharmaceutically acceptable salt thereof of the present invention are useful for treating or preventing chronic obstructive pulmonary diseases, particularly chronic pulmonary emphysema; iritis; proliferative vitreoretinopathy; psoriasis; inflammatory intestinal diseases, particularly Crohn's diseases; hepatitis; superficial pain on congelation, burn, herpes zoster or diabetic neuropathy; tenalgia attended to hyperlipidemia; postoperative neuroma, particularly of mastectomy; vulvar vestibulitis; hemodialysis-associated itching; lichen planus; larvngopharyngitis; bronchiectasis; coniosis; whooping cough; pulmonary tuberculosis; cystic fibrosis; emesis; mental diseases, particularly anxiety, depression, dysthymic disorders and schizophrenia; demyelinating diseases such as multiple sclerosis and amyotrophic lateral sclerosis; attenuation of morphine withdrawal; oedema, such as oedema caused by thermal injury; small cell carcinomas, particularly small cell lung cancer (SCLC); hypersensitivity disorders such as poison ivy; fibrosing and collagen diseases such as scleroderma and eosinophilic fascioliasis; reflex sympathetic dystrophy such as shoulder/hand syndrome; addiction disorders such as alcoholism; stress related somatic disorders; rheumatic diseases such as fibrositis; and the like.

For therapeutic purpose, the compound (I) and a pharmaceutically acceptable salt thereof of the present invention can be used in a form of pharmaceutical preparation containing one of said compound, as an active ingredient, in admixture with a pharmaceutically acceptable carrier such as an organic or inorganic solid or liquid excipient suitable for oral, parenteral, external including topical, enteral, intravenous, intramuscular, inhalant, nasal, intraarticular, intraspinal, transtracheal or transocular administration. The pharmaceutical preparations may be solid, semi-solid or solutions such as capsules, tablets, pellets, dragees, powders, granules, suppositories, ointments, creams, lotions, inhalants, injections, cataplasms, gels, tapes, eye drops, solution, syrups, aerosols, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of a patient, an average single dose of about 0.1 mg, 1 mg, 10 mg, 50 mg, 100 mg, 250 mg, 500 mg and 1000 mg of the compound (I) may be effective for treating Tachykinin-mediated diseases such as asthma and the like. In general, amounts between 0.1 mg/body and about 1,000 mg/body may be administered per day.

In order to illustrate the usefulness of the object compound (I) and a pharmaceutically acceptable salt thereof, the pharmacological test data of some representative compounds of the present invention is shown in the following.

All of the following Test Compounds showed more than 90% inhibition rate of $^{125}$I-BH-Substance P binding to h-NK$_1$, receptors at the concentration of 0.1 μg/ml.

Test Compounds : The object compounds of the Examples 2, 3, 5, 6, 7-1, 7-3 and 7-4

$^{125}$I-BH-Substance P Binding to h-NK$_1$ Receptors

Test Method : $^{125}$I-BH-Substance P Binding to h-NK$_1$ Receptors (a) Crude CHO cell membrane preparation CHO cells permanently expressing h-NK$_1$ receptors were harvested and homogenized with a Dounce homogenizer at 4° C. in a buffer (0.25 M sucrose, 25 nM Tris-HCl pH 7.4, 10 mM MgCl$_2$, 1 mM EDTA, 5 μg/ml p-APMSF). The homogenate was centrifuged (500×g, 10 minutes), and the pellet was resuspended in the same buffer, homogenized, and centrifuged. The two supernatants were combined and centrifuged (100,000×g, 1 hour). The crude cell membranes thus isolated were resuspended in buffer (25 mM Tris-HCl pH 7.4, 10 mM MgCl$_2$, 1 mM EDTA, 5 μg/ml p-APMSF) and stored at −80° C. until use.

(b) $^{125}$I-BH-Substance P binding to preparation membrane

Cell membranes (6 μg/mi) were incubated with $^{125}$I-BH-Substance P (0.1 nM) with or without test compounds in 0.25 ml of Medium 2(50 mM Tris-HCl pH 7.4, 5 mM MnCl$_2$, 20 μg/ml chymostatin, 40 μg/ml bacitracin, 4 μg/ml leupeptin, 5 μg/ml p-APMSF, 200 μg/ml BSA) at 22° C. for 90 minutes. At the end of the incubation period, the content was quickly filtered over a Wahtman GF/C glass filter (pretreated with 0.1% polyethylene imine for 3 hours prior to use) under aspiration. Each of the filters was then washed four times with 5 ml of buffer (50 mM Tris-HCl pH 7.4, 5 mM MnCl$_2$). The radioactivity was counted by using Auto Gamma counter (Packerd RIASTAR 5420A). All data presented are specific binding defined as that displaceable by 3 μM unlabeled Substance P.

The following Preparations and Examples are given for the purpose of illustrating this invention.

Preparation 1

To a solution of (1R)-N$^1$-(tert-butoxycarbonyl)-1-(1H-indol-3-ylmethyl)-1,2-ethanediamine (1.00 g) in N,N'-dimethylpropyleneurea (10 ml) were added successively ethyl 4-bromobutyrate (0.49 ml) and sodium carbonate (0.73 g) at room temperature in a stream of nitrogen. The mixture was stirred at the same temperature for 45 minutes and then at 110° C. for 3 hours. After cooling to room temperature, water (100 ml) and diethyl ether (50 ml) were added into the mixture. The organic layer was separated and washed with brine, and dried over magnesium sulfate. After evaporation in vacuo, the residue was purified by column chromatography on silica gel (35 g) eluting with a mixture of dichloromethane-methanol (from 0% to 6% gradient solution) to give (1R)-N$^1$-(tert-butoxycarbonyl)-N$^2$-[3-(ethoxycarbonyl)-propyl]-1-(1H-indol-3-ylmethyl)-1,2-ethanediamine (0.78 g) as an oil.

IR (Neat): 3310, 2960, 2920, 1685 cm$^{-1}$ NMR (DMSO-d$_6$, δ) 1.16 (3H, t, J=7.1 Hz); 1.15–1.30 (1H, m); 1.36 (9H, s); 1.51–1.72 (2H, m); 2.30 (2H, t, J=7.3 Hz); 2.38–2.58 (4H, m); 2.67–2.93 (2H, m); 3.62–3.82 (1H, m); 4.03 (2H, q, J=7.1 Hz); 6.61 (1H, d, J=7.9 Hz); 6.92–7.14 (3H, m); 7.31 (1H, d, J=7.5 Hz); 7.57 (1H, d, J=7.4 Hz); 10.77 (1H, s) MASS: 404 (M+1)

Preparation 2

To an ice-cooled solution of (1R)-N$^1$-(tert-butoxycarbonyl)-1-(1H-indol-3-ylmethyl)-1,2-ethanediamine (7.00 g) in a mixed solvent of dichloromethane (200 ml) and dimethylformamide (200 ml) was added potassium carbonate (10.03 g). To the mixture was added dropwise bromoacetyl chloride (7.61 g) for 3 minutes, and then the mixture was stirred at the same temperature for 1 hour and 40 minutes by adding further potassium carbonate (3.34 g) and bromoacetyl chloride (2.00 ml) into the mixture. The resulting mixture was poured into water, and extracted twice with dichloromethane. The extracts were combined and washed successively with 0.5N hydrochloric acid and brine, and dried over magnesium sulfate. After evaporation in vacuo, the residue was dried to give (1R)-N$^1$-(tert-butoxycarbonyl)-N$^2$-(bromoacetyl)-1-(1H-indol-3-ylmethyl)-1,2-ethanediamine (9.9 g) as crystal.

IR (Nujol) 3300, 1654–1633, 1522 cm$^{-1}$ NMR (DMSO-d$_6$, δ): 1.17, 1.35 (9H, 2 s); 2.65–2.94 (2H, m); 3.00–3.34 (2H, m); 3.66–3.85 (1H, m); 3.86, 4.06 (2H, 2 s); 6.64–6.75 (1H, m); 6.92–7.62 (5H, m); 8.12–8.41 (1H, m); 10.81 (1H, s)

Preparation 3

(1R)-N$^1$-(tert-Butoxycarbonyl)-N$^2$-(bromoacetyl)-N$^2$-[3-(ethoxycarbonyl)propyl]-1-(1H-indol-3-ylmethyl)-1,2-ethanediamine (0.95 g) was obtained as an oil from the object compound of the Preparation 1 (0.74 g) according to a similar manner to that of the Preparation 2.

IR (Neat): 3280, 2920, 1655 cm$^{-1}$ NMR (DMSO-d$_6$, δ): 1.05–1.25 (3H, m); 1.29, 1.31 (9H, 2 s); 1.54–1.89 (2H, m); 2.11–2.41 (2H, m); 2.67–3.52 (7H, m); 3.84–4.37 (4H, m); 6.80–7.61 (6H, m); 10.79, 10.82 (1H, 2 s)

Preparation 4

To an ice-cooled solution of (1R)-N$^1$-(tert-butoxycarbonyl)-N$^2$-(bromoacetyl)-1-(1H-indol-3-ylmethyl)-1,2-ethanediamine (9.32 g) in ethyl acetate (90 ml) was added 4N hydrogen chloride in ethyl acetate solution (90 ml). The mixture was stirred at the same temperature for 50 minutes and then evaporated under reduced pressure. Dichloromethane and aqueous saturated sodium bicarbonate solution were added to the residue. The organic layer was separated. The aqueous layer was extracted six times with dichloromethane. The extracts were combined and dried over magnesium sulfate, and concentrated under reduced pressure to give (1R)-N$^2$-(bromoacetyl)- 1-(1H-indol-3-ylmethyl)-1,2-ethanediamine (3.01 g) as an oil.

IR (Neat): 3230, 2910, 1650, 1523 cm$^{-1}$ NMR (DMSO-d$_6$, δ): 2.66–3.68 (5H, m); 4.12 (2H, s); 6.88–8.58 (6H, m); 10.90 (1H, s)

Preparation 5

(1R)-N$^2$-(Bromoacetyl)-N$^2$-[3-(ethoxycarbonyl)propyl]-1-(1H-indol-3-ylmethyl)-1,2-ethanediamine (0.76 g) was obtained as an oil from the object compound of the Preparation 3 (0.95 g) according to a similar manner to that of the Preparation 4.

IR (Neat): 3220, 2910, 1720, 1654 cm$^{-1}$ NMR (DMSO-d$_6$, δ): 1.08–1.31 (5H, m); 1.57–1.95 (2H, m); 2.13–2.45 (2H, m); 2.80–3.82 (8H, m); 3.94–4.15 (3H, m); 6.91–7.66 (5H, m); 10.92, 11.04 (1H, 2 s)

Preparation 6

To a solution of (1R)-N$^2$-(bromoacetyl)-1-(1H-indol-3-ylmethyl)-1,2-ethanediamine (3.30 g) in dimethylformamide (70 ml) was added potassium carbonate (3.30 g) at room temperature. The reaction mixture was stirred at 110° C. for 1 hour and 20 minutes. After cooling to room temperature, water and dichloromethane were added into the mixture, and the organic layer was separated. The aqueous layer was extracted successively with dichloromethane several times and a mixed solvent of ethyl acetate and methanol (10:1). The extracts were combined and dried over magnesium sulfate, and concentrated under reduced pressure to give (5R)-5-(1H-indol-3-ylmethyl)piperazin-2-one (2.47 g) as an oil.

IR (Neat): 3230, 2910, 1655–1635 cm$^{-1}$ NMR (DMSO-d$_6$, δ): 2.60–3.47 (8H, m); 6.86–7.60 (5H, m); 7.95 (1H, s); 10.87 (1H, s) MASS: 230 (M+1)

Preparation 7

(5R)-1-[3-Ethoxycarbonyl)propyl]-5-(1H-indol-3-ylmethyl)piperazin-2-one (0.60 g) was obtained as an oil from the object compound of the Preparation 5 (0.79 g) according to a similar manner to that of the Preparation 6.

IR (Neat): 3240, 2920, 1718, 1653–1624 cm$^{-1}$ NMR (DMSO-d$_6$, δ): 1.15 (3H, t, J=7.1 Hz); 1.10–1.27 (1H, m); 1.57–1.78 (2H, m); 2.17–2.35 (2H, m); 2.73–3.65 (9H, m); 4.02 (2H, q, t=7.1 Hz); 6.91–7.23 (3H, m); 7.55 (1H, d, j=7.7 Hz); 7.55 (1H, d, J=7.7 Hz); 10.88 (1H, s) MASS: 344 (M+1)

EXAMPLE 1

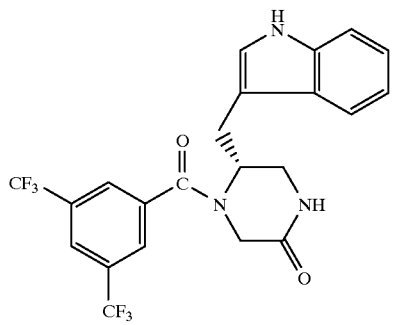

To a solution of 3,5-bis(trifluoromethyl)benzoic acid (2.63 g) and (5R)-5-(1H-indol-3-ylmethyl)piperazin-2-one (2.34 g) in dichloromethane (50 ml) were added successively triethylamine (3.56 ml) and 2-chloro-1-methylpyridinium iodide (3.13 g) at room temperature. The resulting mixture was stirred for 1.5 hours at the same temperature. Dichloromethane and water were added into the mixture and the organic layer was separated. The organic layer was washed successively with 0.5N hydrochloric acid, water, aqueous sodium bicarbonate solution and brine, and dried over magnesium sulfate. After evaporation in vacuo, the residue was purified by column chromatography on silica gel (75 g) eluting with a mixture of dichloromethane-methanol (from 0% to 5% gradient elution) to give (5R)-4-[3,5-bis(trifluoromethyl)benzoyl]-5-(1H-indol-3-ylmethyl)piperazin-2-one (1.25 g) as an oil.

IR (Neat): 3260, 3050, 3000, 2910, 1670–1634, 1570 cm$^{-1}$ NMR (DMSO-d$_6$, δ): 2.79–3.46 (4H, m); 3.64–4.11 (1H, m); 3.99 (1H, d, J=18.6 Hz); 4.35 (1H, d, J=19.0 Hz); 6.57–8.27 (9H, m); 10.91 (1H, s) MASS: 470 (M+1)

EXAMPLE 2

To an ice-cooled solution of (5R)-5-(1H-indol-3-ylmethyl)-1-[3-(ethoxycarbonyl)propyl]piperazin-2-one (0.56 g) and pyridine (0.26 ml) in dichloromethane (10 ml) was added a solution of 3,5-bis(trifluoromethyl)benzoyl chloride (0.45 g) in dichloromethane (1 ml). The solution was stirred for 40 minutes at the same temperature. After concentration, the residue was extracted with ethyl acetate. The organic layer was washed successively with aqueous sodium bicarbonate solution, water, 0.5N hydrochloric acid and brine, and dried over magnesium sulfate, and concentrated in vacuo. The residue was purified by column chromatography on silica gel (20 g) eluting with a mixture of dichloromethane-methanol (from 0% to 5% gradient solution) to give (5R)-4-[3,5-bis(trifluoromethyl)benzoyl]-1-[3-(ethoxycarbonyl)propyl]-5-(1H-indol-3-ylmethyl)piperazin-2-one (0.34 g) as an amorphous solid.

IR (Neat): 3280, 2910, 1720, 1635 cm$^{-1}$ NMR (DMSO-d$_6$, δ): 1.18 (3H, t, J=7.1 Hz); 1.60–1.83 (2H, m); 2.37 (2H, t, J=7.3 Hz); 2.77–3.63 (6H, m); 4.06 (2H, t, J=7.1 Hz); 3.67–5.15 (3H, m); 6.55–8.55 (8H, m); 10.89 (1H, s) MASS: 584 (M+1)

EXAMPLE 3

To an ice-cooled solution of (5R)-4-[3,5-bis(trifluoromethyl)benzoyl]-5-(1H-indol-3-ylmethyl)piperazin-2-one (2.15 g) in tetrahydrofuran (43 ml) were added successively sodium hydride (60%) (0.37 g) and ethyl bromoacetate (0.56 ml) in a stream of nitrogen. The mixture was stirred for 55 minutes at the same temperature, and water (20 ml) and 0.5N hydrochloric acid (20 ml) were added successively to the mixture. After stirring for 10 minutes, dichloromethane (80 ml) was added into the mixture at room temperature and the organic layer was separated. The organic layer was washed with brine, and dried over magnesium sulfate. After evaporation in vacuo, the residue was purified by column chromatography on silica gel (60 g) eluting with a mixture of dichloromethane-methanol (from 0% to 2% gradient solution) to give (5R)-4-[3,5-bis(trifluoromethyl)benzoyl]-1-(ethoxycarbonylmethyl)-5-(1H-indol-3-ylmethyl)piperazin-2-one (1.20 g) as an amorphous solid.

[α]$^{26}_D$: 2.9° (C=1.0, CHCl$_3$) IR (Neat): 3310, 2970, 2910, 1737, 1655–1635 cm$^{-1}$ NMR (DMSO-d$_6$, δ): 1.24 (3H, t, J=7.1 Hz); 2.87–5.14 (11H, m); 6.55–8.29 (8H, m); 10.91 (1H, s) MASS: 556 (M+1)

EXAMPLE 4

To an ice-cooled solution of (5R)-4-[3,5-bis(trifluoromethyl)benzoyl]-1-(ethoxycarbonylmethyl)-5-(1H-indol-3-ylmethyl)piperazin-2-one (0.88 g) in ethanol (20 ml) was added 1N sodium hydroxide solution (1.58 ml). The mixture was stirred at the same temperature for 30 minutes and then at room temperature for 1 hour and 45 minutes. The mixture was concentrated under reduced pressure, and water and 1N hydrochloric acid (1.58 ml) were added to the residue under ice-cooling. The mixture was extracted with ethyl acetate. The organic layer was washed with brine, and dried over magnesium sulfate. After evaporation in vacuo, n-hexane was added to the crystalline residue and the resulting crystals were collected by filtration, washed with n-hexane, and dried to give (5R)-4-[3,5-bis(trifluoromethyl)benzoyl]-1-(carboxymethyl)-5-(1H-indol-3-ylmethyl)piperazin-2-one (0.76 g).

mp: >220° C. IR (Nujol): 3450, 1732, 1653, 1600, 1508 cm$^{-1}$ NMR (DMSO-d$_6$, δ): 2.87–5.16 (9H, m); 6.53–8.28 (8H, m); 10.90 (1H, s); 12.90 (1H, br s) MASS: 528 (M+l)

EXAMPLE 5

To an ice-cooled solution of (5R)-4-[3,5-bis(trifluoromethyl)benzoyl]-1-(carboxymethyl)-5-(1H-indol-3-ylmethyl)piperazin-2-one (0.15 g) and 1-hydroxybenzotriazole (0.038 g) in dichloromethane (3 ml) was added 1-(3-dimethylaminopropyl)-3-ethylcarbodiimide hydrochloride (0.055 g). After the solution was stirred for 2 hours and 55 minutes at the same temperature, 28% aqueous ammonia solution (0.017 ml) was added into the mixture under ice-cooling. The mixture was stirred for 2 hours and 25 minutes at room temperature. After evaporation of the solvent, the residue was extracted with ethyl acetate. The organic layer was washed successively with aqueous sodium bicarbonate solution, water and brine, and dried over magnesium sulfate. After evaporation in vacuo, the residue was purified by column chromatography on silica gel (10 g) eluting with a mixture of dichloromethane-methanol (from 0c to 5% gradient solution). To the eluate containing objective product was added diisopropyl ether and the resulting precipitates were collected by filtration, washed with diisopropyl ether, and dried to give (5R)-4-[3,5-bis(trifluoromethyl)benzoyl]-1-(carbamoylmethyl)-5-(1H-indol-3-ylmethyl)piperazin-2-one (0.10 g) as an amorphous solid.

IR (Nujol): 3290, 1634 cm$^{-1}$ NMR (DMSO-d$_6$, δ): 2.89–5.08 (9H, m); 6.55–8.27 (10H, m); 10.90 (1H, s) MASS: 527 (M+l)

EXAMPLE 6

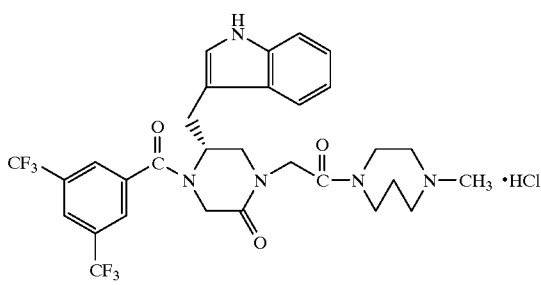

To an ice-cooled solution of (5R)-4-[3,5-bis(trifluoromethyl)benzoyl]-1-(carboxymethyl)-5-(1H-indol-3-ylmethyl)piperazin-2-one (0.15 g), 1-methylhomopiperazine (0.032 g) and 1-hydroxybenzotriazole (0.038 g) in dichloromethane (3 ml) was added 1-(3-dimethylaminopropyl)-3-ethylcarbodiimide hydrochloride (0.055 g). The mixture was stirred at the same temperature for 1 hour and then at room temperature for 16 hours. Water and aqueous sodium bicarbonate solution were added and then the resulting mixture was extracted with dichloromethane. The organic layer was washed successively with aqueous sodium bicarbonate solution, water and brine, and dried over magnesium sulfate. After evaporation in vacuo, the residue (0.13 g) was dissolved in dichloromethane (2 ml). To the solution was added 4N hydrogen chloride in dioxane solution (0.052 ml) under ice-cooling, and the mixture was stirred for 50 minutes at the same temperature. After concentration, ether was added to the residue and the resulting precipitates were collected by filtration, washed with ether, and dried to give (5R)-4-[3,5-bis(trifluoromethyl)benzoyl]-5-(1H-indol-3-ylmethyl)-1-[[(4-methyl-1-homopiperazinyl)carbonylmethyl]-piperazin-2-one hydrochloride (0.13 g) as an amorphous solid.

mp: 175–190° C. IR (Nujol): 3470, 3180, 1654, 1637 cm$^{-1}$ NMR (DMSO-d$_6$, δ): 1.96–2.43 (2H, m); 2.77 (3H, s); 2.90–5.16 (15H, m); 4.11 (1H, d, J=18.3 Hz); 4.49 (1H, d, J=18.9 Hz); 6.55–8.30 (8H, m); 10.94 (1H, s); 10.94 (1H, br s) MASS: 624 (M+1) (free)

EXAMPLE 7

The following object piperazine derivatives (Table) were prepared by the similar manner to that of the each Example No. defined in the "Process" column from the obtained compound of the each Example No. defined in the "Starting Compound" column. The physical properties of the object compounds are shown after the table.

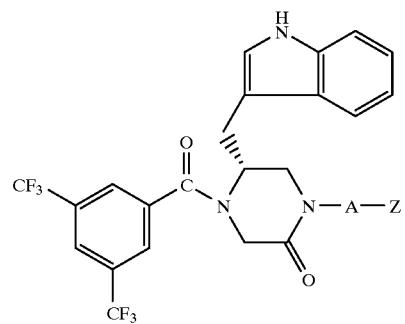

TABLE

| Example No. | A | Z | Salt | Starting Compound | Process |
|---|---|---|---|---|---|
| 7-1) | —CH$_2$— | —C(O)—N(piperidine-piperidine) | HCl | Ex. 4 | Ex. 6 |
| 7-2) | —CH$_2$— | —C(O)—NH—N(piperazine)—CH$_3$ | 2HCl | Ex. 4 | Ex. 6 |
| 7-3) | —(CH$_2$)$_3$— | —C(O)—N(piperidine-piperidine) | HCl | Ex. 7-5) | Ex. 6 |

TABLE-continued

| Example No. | Object Compounds A | Z | Salt | Starting Compound | Process |
|---|---|---|---|---|---|
| 7-4) | —(CH$_2$)$_3$— | 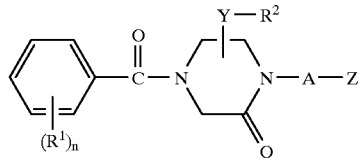 | HCl | Ex. 7-5) | Ex. 6 |
| 7-5) | —(CH$_2$)$_3$ | —C(=O)—OH | — | Ex. 2 | Ex. 4 |

Physical properties of the compounds of the Example 7:

EXAMPLE 7-1)

IR (Nujol): 3350, 2640, 2520, 1632 cm$^{-1}$ NMR (DMSO-d$_6$, δ): 1.30–2.30 (10H, m); 2.52–5.12 (16H, m); 4.11 (1H, d, J=18.4 Hz); 4.47 (1H, d, J=19.0 Hz); 6.56–8.29 (8H, m); 10.31 (1H, br s); 10.93 (1H, s) MASS: 678 (M+1) (free)

EXAMPLE 7-2)

IR (Nujol): 3350–3250, 2680, 1632 cm$^{-1}$ NMR (DMSO-d$_6$, δ): 2.74, 2.76 (3H, 2 s); 2.90–5.10 (17H, m); 6.55–8.26 (8H, m); 9.08, 9.57 (1H, 2 s); 10.87–11.00 (1H, m); 10.93 (1H, s) MASS: 625 (M+1) (free)

EXAMPLE 7-3)

IR (Nujol): 3370–3220, 2680, 1630 cm$^{-1}$ NMR (DMSO-d$_6$, δ): 1.20–5.15 (32H, m); 6.57–8.29 (8H, m); 10.33 (1H, br s); 10.94 (1H, s) MASS: 706 (M+1) (free)

EXAMPLE 7-4)

IR (Nujol): 3350–3250, 2650, 1620 cm$^{-1}$ NMR (DMSO-d$_6$, δ): 1.68–2.48 (6H, m); 2.76 (3H, s); 2.85–5.14 (17H, m); 6.58–8.28 (8H, m); 10.70 (1H, br s); 10.95 (1H, s) MASS: 652 (M+1) (free)

EXAMPLE 7-5)

IR (Neat): 3290, 2910, 1717, 1631 cm$^{-1}$ NMR: (DMSO-d$_6$, δ): 1.60–1.90 (2H, m); 2.30 (2H, t, j=7.3 Hz); 2.80–5.18 (9H, m); 6.56–8.48 (8H, m); 10.91 (1H, s); 12.12 (1H, s) MASS: 556 (m+1)

We claim:

1. A compound of the following general formula:

[Structure: benzene ring with (R$^1$)$_n$ substituents, connected via —C(=O)—N— to a piperazinone ring bearing Y—R$^2$ substituent and N—A—Z]

wherein
Y is lower alkylene;
R$^1$ is halo (lower) alkyl;
R$^2$ is indolyl;
A is bond or lower alkylene;
Z is hydrogen, carboxy, lower alkoxycarbonyl or a group of the formula:

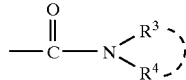

in which
R$^3$ and R$^4$ are independently hydrogen; or
1-pyrrolidinyl, 1-piperidyl, 4-inorpholino, 1-piperazinyl or 1-homopiperazinyl, each of which may be substituted by 1, 2 or 3 substituent(s) selected from the group consisting of lower alkyl, 1-pyrrolidinyl, 1-piperidyl, 4-morpholino, 1-piperazinyl and 1-homopiperazinyl, or R$^3$ and R$^4$ together with the adjacent nitrogen atom form 1-pyrrolidinyl, 1-piperidyl, 4-morpholino, 1-piperazinyl or 1-homopiperazinyl, each of which may be substituted by 1, 2 or 3 substituent(s) selected from the group consisting of lower alkyl, 1-pyrrolidinyl, 1-piperidyl, 4-morpholino, 1-piperazinyl and 1-homopiperazinyl; and
n is 2,
or its pharmaceutically acceptable salt.

2. The compound of claim 1, in which
Y is (C$_1$–C$_4$) alkylene;
R' is halo (C$_1$–C$_4$) alkyl;
R$^2$ is indolyl;
A is bond or (C$_1$–C$_4$) alkylene;
Z is hydrogen, carboxy, (C$_1$–C$_4$) alkoxycarbonyl or a group of the formula:

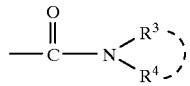

in which
R$^3$ and R$^4$ are independently hydrogen; or
1-pyrrolidinyl, 1-piperidyl, 4-inorpholino, 1-piperazinyl or 1-homopiperazinyl, each of which may be substituted by a substituent selected from the group consisting of (C$_1$–C$_4$) alkyl, 1-pyrrolidinyl, 1-piperidyl, 4-morpholino, 1-piperazinyl and 1-homopiperazinyl, or R$^3$ and R$^4$ together with the adjacent nitrogen atom form 1-pyrrolidinyl, 1-piperidyl, 4-morpholino, 1-piperazinyl or 1-homopiperazinyl, each of which may be substituted by a substituent selected from the group consisting of (C$_1$–C$_4$) alkyl, 1-pyrrolidinyl, 1-piperidyl, 4-morpholino, 1-piperazinyl and 1-homopiperazinyl; and n is 2.

3. The compound of claim 2, in which

Y is methylene;

$R^1$ is trifluoromethyl;

$R^2$ is indolyl;

A is bond, methylene or trimethylene;

Z is hydrogen, carboxy, ($C_1$–$C_4$) alkoxycarbonyl or a group of the formula:

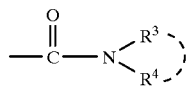

in which $R^3$ and $R^4$ are independently hydrogen or piperazinyl which may be substituted by ($C_1$–$C_4$) alkyl; or $R^3$ and $R^4$ together with the adjacent nitrogen atom form 1-piperidyl which may be substituted by piperidyl, or 1-homopiperazinyl which may be substituted by ($C_1$–$C_4$) alkyl; and n is 2.

4. A process for the preparation of compound of the following general formula:

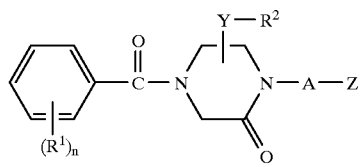

wherein

Y is ($C_1$–$C_4$) alkylene;

$R^1$ is halo ($C_1$–$C_4$) alkyl;

$R^2$ is indolyl;

A is bond or ($C_1$–$C_4$) alkylene;

Z is hydrogen, carboxy, ($C_1$–$C_4$) alkoxycarbonyl or a group of the formula:

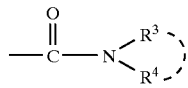

in which $R^3$ and $R^4$ are independently hydrogen; or 1-pyrrolidinyl, 1-piperidyl, 4-morpholino, 1-piperazinyl or 1-hoinopiperazinyl, each of which may be substituted by a substituent selected from the group consisting of ($C_1$–$C_4$) alkyl, 1-pyrrolidinyl, 1-piperidyl, 4-morpholino, 1-piperazinyl and 1-homopiperazinyl, or $R^3$ and $R^4$ together with the adjacent nitrogen atom form 1-pyrrolidinyl, 1-piperidyl, 4-morpholino, 1-piperazinyl or 1-homopiperazinyl, each of which may be substituted by a substituent selected from the group consisting of ($C_1$–$C_4$) alkyl, 1-pyrrolidinyl, 1-piperidyl, 4-morpholino, 1-piperazinyl and 1-homopiperazinyl; and n is 2;

or its salt, which comprises reacting a compound of the formula:

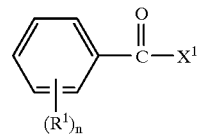

or a salt thereof with a compound of the formula:

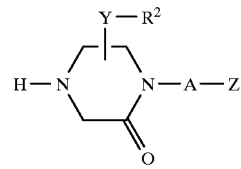

or its reactive derivative at the imino group or a salt thereof to give a compound of the formula:

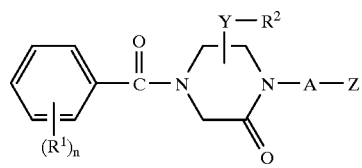

or a salt thereof, in the above formulas, A, Y, Z, $R^1$, $R^2$ and n are each as defined above, and $X^1$ is hydroxy or halogen.

5. A pharmaceutical composition comprising a compound of claim 1 as an active ingredient, in association with a pharmaceutically acceptable, substantially non-toxic carrier or excipient.

* * * * *